United States Patent [19]

Abiko et al.

[11] Patent Number: 4,846,168

[45] Date of Patent: Jul. 11, 1989

[54] INHALER

[75] Inventors: Kenji Abiko, Kaminoyama; Shikoh Minagawa; Hiroshi Shinohara, both of Yamagata; Kayoko Koseki, Nanyo, all of Japan

[73] Assignee: MECT Corporation, Tokyo, Japan

[21] Appl. No.: 127,490

[22] Filed: Dec. 1, 1987

[30] Foreign Application Priority Data

Dec. 5, 1986 [JP] Japan ................................ 61-291163

[51] Int. Cl.[4] ............................................ A61M 15/00

[52] U.S. Cl. .......................... 128/203.15; 128/200.23

[58] Field of Search ...................... 128/203.12, 203.13, 128/203.14, 203.15, 203.19, 203.21, 203.23, 200.18, 200.23; 604/58; D24/62

[56] References Cited

U.S. PATENT DOCUMENTS

| | | | |
|---|---|---|---|
| 2,470,296 | 5/1949 | Fields | 128/203.15 |
| 2,470,297 | 5/1949 | Fields | 128/203.15 |
| 3,027,897 | 4/1962 | Carofiglio | 128/203.23 |
| 3,170,462 | 2/1965 | Hall | 128/200.23 |
| 3,938,516 | 2/1976 | Mathes | 128/203.15 |
| 3,973,566 | 8/1976 | Mathes | 128/203.15 |
| 3,980,074 | 4/1976 | Watt et al. | 128/203.15 |
| 4,098,273 | 7/1978 | Glenn | 128/203.15 |
| 4,105,027 | 8/1978 | Lundquist | 128/203.15 |
| 4,137,914 | 2/1979 | Wetterlin | 128/200.23 |
| 4,206,758 | 6/1980 | Hallworth et al. | 128/203.15 |
| 4,353,365 | 10/1982 | Hallworth et al. | 128/203.15 |
| 4,641,644 | 2/1987 | Andersson et al. | 128/200.23 |

*Primary Examiner*—Edgar S. Burr
*Assistant Examiner*—Kimberly L. Asher
*Attorney, Agent, or Firm*—Rodman & Rodman

[57] ABSTRACT

An inhaler in use for inhaling pharmaceutical powdered preparations through the mouth and making the same reach a trachea, bronchi and pulmonary cells. The inhaler has a generally bent form with a predetermined bend angle, preferably, at 60 degrees. The inhaler includes a hollow body, a capsule holding portion for receiving and holding a capsule, and an inhaling section. The capsule holding portion is rotated relative to a hollow body, whereby the capsule is divided into two including a barrel and a head, so that the powdered preparations can fall into the hollow body. The powdered preparations, which have fallen into the hollow body can be inhaled into a human body together with intake air flowing through air intake openings provided in the capsule holding portion by mouth suction applied to the inhaling section. The capsule barrel which has fallen into the hollow body is prevented from being inhaled into the human body due to the presence of a porous member.

18 Claims, 7 Drawing Sheets

INHALER

BACKGROUND OF THE INVENTION

1. Field of the Invention

This invention relates to inhalers, particularly to an inhaler used for inhaling pharmaceutical powdered preparations so as to enable such preparations to reach a trachea, bronchi and pulmonary cells.

2. Related Art Statement

In general, in order to distribute pharmaceutical preparations into an oral cavity of the human body to reach the trachea, bronchi and pulmonary cells of a human body, there has been known use of an atomizing type spraying device. However, with the device of this type, patients tend to close the deep portion of the oral cavity instinctively or in a conditioned response at the moment of spraying, so that it has been difficult to accomplish the desired objective.

Therefore, to obviate the above-described disadvantage, there have been proposed inhalers for smoothly inhaling the pharmaceutical powdered preparations into the trachea, bronchi and pulmonary cells to accompany the inspiration of air by a patient.

As one of these inhalers, disclosed in Japanese Patent Laid-Open No. 53-136392, comprises: a straight-lined hollow barrel body formed with a chamber and provided at a side surface thereof with air intake openings that communicate with the chamber; and a lid sleeve connected to one end of this barrel body, having a capsule holding sleeve and being rotatable relative to the barrel body. When the barrel body and the lid sleeve are rotated relative to each other, a capsule insertion portion held by the capsule holding sleeve is engaged with an abutting portion in the barrel body, whereby the capsule is divided into a capsule barrel and a capsule head. The powdered preparations contained in the capsule are dropped into the chamber and inhaled into an oral cavity of the patient through a nozzle.

Furthermore, in a magazine "The Practitioner" March, 1982 issue, 226th volume, pages 565-567, there is disclosed an inhaler comprising: a straight-lined hollow inner barrel; and an outer barrel connected to one end of the inner barrel and rotatable relative to the inner barrel. The outer barrel is provided at one end with a capsule insertion hole and air intake openings. When the inner barrel is rotated relative to the outer barrel, a capsule insertion portion is engaged with an abutting portion in the inner barrel, so that a capsule is divided into a main body and a head and powdered preparations which fall into the inner barrel are inhaled from the other end of the inner barrel.

However, it has become apparent from studies made by the inventors of the present invention that the above-described two inventions of the prior art present serious problems when used as the inhaler.

First, the former, i.e. the invention of the prior art disclosed in the Japanese Patent Laid-Open No. 53-136392 presents the following problems.

(1) The inhaler as a whole is of a straight-line form. When the capsule is divided into a main body and the head thereof by the rotation of the hollow barrel body and the lid sleeve relative to each other, the powdered preparations which have fallen into the hollow barrel body may leak out of the hollow barrel body to the outside. Because of this, shortage or waste of the contained material may result. This problem is particularly notable because the capsule insertion hole is positioned at a location very close to the nozzle for inhaling.

(2) The air flow-in openings for the hollow barrel body are formed in the side surface, and the end face is blocked. Thus ideal turbulent flows are difficult to obtain in the chamber and the operating maneuvers of the capsule barrel which has fallen into the chamber are not briskly performed. Accordingly, the powdered preparations in the capsule barrel are difficult to discharge into the hollow barrel body, and further, the powdered preparations which have fallen into the chamber cannot be efficiently inhaled out of the chamber. Thus the powdered preparations remain in the capsule, and moreover, in the chamber. Therefore, an expected remedial result cannot be achieved due to the shortage of the planned dosage.

(3) Since the capsule holding sleeve is provided at a position very close to the inhaling nozzle, the capsule disturbs the patient when inhaling nozzle is put in his mouth to perform inhalation.

(4) Since the general form of the inhaler is of a straight-line cylindrical form, there is a possibility that the inhaler will roll off a flat surface such as a table.

Possibly due to the above-described serious disadvantages, the inhaler of the type described has not heretofore been put on the market as a product.

Next, the latter invention of the prior art presents the following serious drawbacks.

(a) The inhaler as a whole is of a straight-line form and the powdered preparations, which fall from the capsule into the inner barrel by the rotation of the inner barrel and the outer barrel relative to each other, leak out of the inner barrel to the outside as in the case of the previously described prior art.

(1) As the result, an insufficient or wasteful dosage of the powdered preparations is caused.

(b) The air flow-in openings for the inhaler are formed in the end face of the outer barrel. However, the inhaler as a whole is of a straight-lined form, whereby ideal turbulent flows are difficult to develop in the inhaler during inhaling. Furthermore the operating maneuvers of the capsule barrel, which has fallen into the inhaler, are not briskly performed. Accordingly, the powdered preparations in the capsule barrel are not smoothly discharged. Moreover, the powdered preparations are not smoothly inhaled through the inhaling nozzle and remain in the inhaler. Furthermore, in this latter invention there is no disclosure of the size, shape or position of the air intake openings.

(c) In connection with Item (b), ideal turbulent flows are difficult to develop in the inhaler. Also the operating maneuvers of the capsule barrel which falls into the inhaler are not easily performed, and the powdered preparations in the capsule barrel are difficult to transfer out of the capsule barrel and thus remain therein. Because of these problems, an insufficient remedial result is obtained due to a shortage of the planned dosage.

(d) Furthermore, it has been determined from experiments made by the inventors of the present invention that the capsule head still held in the capsule insertion hole of the outer barrel after the capsule barrel is separated therefrom is open at the opening end thereof to the inhaler. Thus, to everyone's surprise, the powdered preparations in the inhaler are recirculated and received again in the capsule head by air streams generated in the inhaler and remain in the capsule head.

(e) Since the general form of the inhaler is of a straight-line cylindrical form, there is a possibility of that the inhaler will roll off a flat surface such as a table.

SUMMARY OF THE INVENTION

The present invention has been developed in response to the above-described problems of the prior art and has as one of its objects the provision of an inhaler for allowing efficient inhalation with no material of the capsule remaining in the inhaler, capsule head and capsule barrel.

Another object of the present invention is to provide an inhaler capable of preventing the material contained in the capsule from leaking out of an inhaling section when the capsule set in the capsule insertion hole is divided into two including the barrel and the head.

According to the present invention, in an inhaler, wherein the hollow body and the capsule holding portion are rotated relative to each other to divide the capsule into the capsule barrel and the capsule head, whereby the material contained in the capsule is made to fall into the inhaler, said hollow body includes a hollow barrel section having a predetermined length and a hollow bent section connected to one end of the hollow barrel section and having an axis inclined at a predetermined angle to an axis of the hollow barrel section.

With the above-described arrangement, the hollow body is of non-straight-line form, whereby the general form of the inhaler is bent, so that turbulent flows is readily developed in the inhaler during inhaling. Accordingly, the material contained in the capsule, which has fallen into the inhaler, is smoothly inhaled to the outside of the inhaler, and does not remain in the inhaler and the capsule, so that a desired inhaling effect can be obtained.

Furthermore, the material contained in the capsule can be effectively prevented from leaking out of the inhaler when the capsule is divided, owing to the bent construction of the inhaler.

BRIEF DESCRIPTION OF THE DRAWINGS

Other objects and merits of the present invention will be apparent from the following description made with reference to the preferred embodiments shown in the drawings, in which.

DETAILED DESCRIPTION OF THE PREFERRED EMBODIMENTS

Embodiment 1

Figure 1:
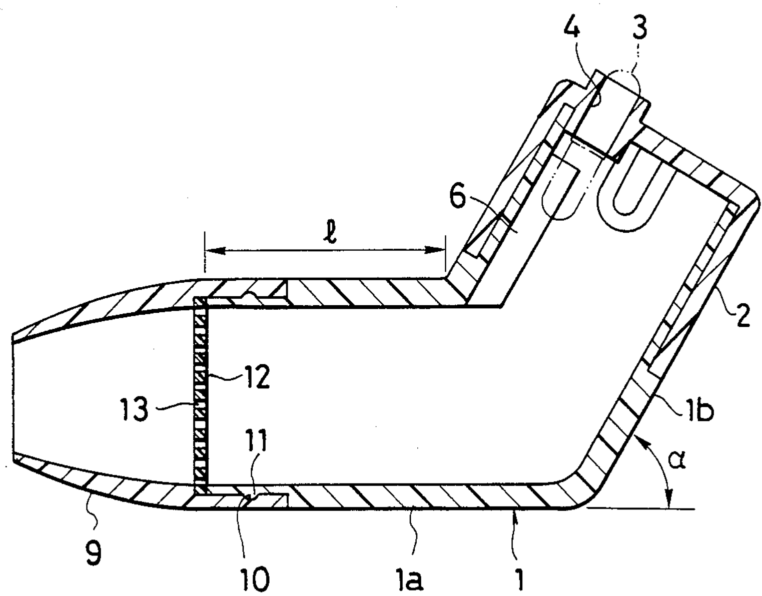
FIG. 1 is a sectional view showing the inhaler in an embodiment 1 of the present invention, taken along the line I—I in FIG. 2.
Figure 2:
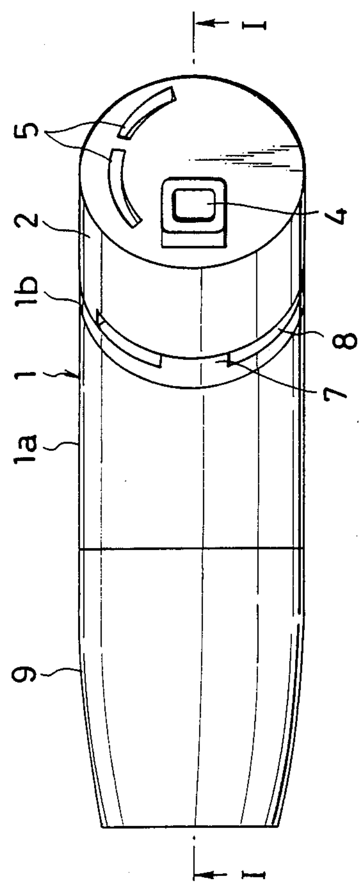
FIG. 2 is a plan view thereof.
Figure 3:
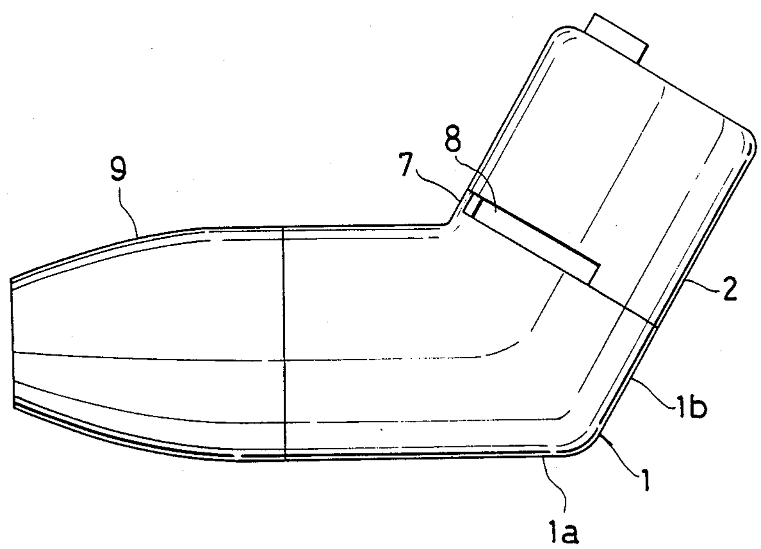
FIG. 3 is a front view thereof.
Figure 4:
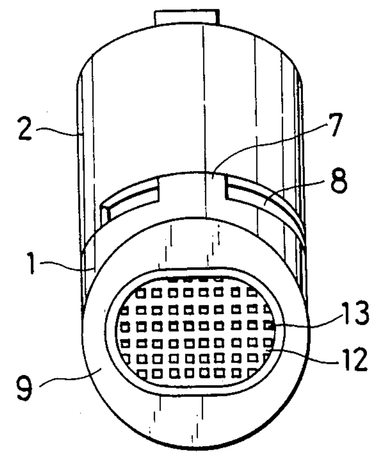
FIG. 4 is a left side view thereof.

Referring now to the drawings, as an example, the inhaler according to this embodiment as a whole can be made of an opaque synthetic resin material. This inhaler has a hollow body 1 including a hollow barrel section 1*a* having a predetermined length l as indicated at the upper position in FIG. 1 and a straight-lined hollow bent section 1*b* formed integrally with this hollow barrel section 1*a* and having an axis inclined at a predetermined angle $\alpha$ to an axis of the hollow barrel section 1*a*.

A generally cup-shaped capsule holding portion 2 formed of a molded part made of a synthetic resin material for example is mounted on one end of the bent section 1*b* of the hollow body 1 in a manner to be rotatable relative to the hollow body 1. As indicated by dotted lines in FIG. 1, formed at the end face of the capsule holding portion 2 is a generally square-shaped capsule insertion hole 4 for receiving and holding a capsule 3 containing a material such for example powdered preparations. The end face of the capsule holding portion 2 also includes two generally arcuate slit-shaped air flow-in openings 5 for allowing intake air to flow into the inhaler.

A capsule head, which is a large diametral side of the capsule 3, is inserted into the capsule insertion hole 4 and held therein. A capsule barrel, which is a smaller diametral side of the capsule 3, projects into the bent section 1*b* of the hollow body 1. An abutting ridge (abutting means) 6 extending at least to a position capable of abutting against the portion of capsule 3 that is inserted and projected into the bent section 1*b*, i.e. the capsule barrel, when the capsule 3 is inserted into the capsule insertion hole 4 and held thereby, is projectingly provided and formed integrally at a portion of the inner surface of the bent section 1*b* of the hollow body 1. Under this arrangement, when the capsule holding portion 2 is rotated relative to the hollow body 1, the abutting ridge 6 abuts against the portion of capsule 3 that is inserted and projected into the inhaler, i.e. the capsule barrel, whereby the capsule barrel is separated from the capsule head, so that the powdered preparations in the capsule 3 can fall into the inhaler. Furthermore, to limit the angle of rotation between the hollow body 1 and the capsule holding portion 2 to a predetermined angle, a raised portion 7 formed at the tail end of the bent section 1*b* extends into a groove 8 formed at one end of the capsule holding portion 2 for a predetermined length in the circumferential direction of the capsule holding portion 2. With this arrangement, the hollow body 1 and the capsule holding portion 2 are rotatable relative to each other within a predetermined angular range for which the raised portion 7 can turn in the groove 8 in the rotating direction. However, an alternative arrangement may be adopted wherein the hollow body 1 and the capsule holding portion 2 are freely rotatable relative to each other over an angle of 360 degrees without providing the raised portion 7 and the groove 8 as described above.

On the other hand, detachably, couplingly connected to an end portion of the hollow barrel section 1*a* of the hollow body 1 is a hollow inhaling section 9 to be held in the mouth of the patient. The patient at the inhaling section 9 to take in air and inhales the powdered preparations which have fallen from the capsule 3 into the inhaler. The inhaling section 9 is detachably connected to the hollow body 1 by engaging an annular groove 11 on the inner periphery of a thin wall portion of the inhaling section 9 with an annular ridge 10 on the outer periphery of a thin wall portion of the hollow body 1. The outer shape of the inhaling section 9 is tapered toward the forward end so that the patient can easily put the inhaling section in his mouth.

Furthermore, a porous plate (capsule discharging preventive means) 12 formed of a molded part made of a synthetic resin material for example is connected to an end face of the hollow body 1 on the side of the inhaling section 9 through adhesive bonding for example. This porous plate 12 has a multitude of pores 13 for ventilating. The pores 13 may have such a size as to allow the powdered preparations as being the material contained in the capsule 3 to pass therethrough freely but not to allow the capsule barrel which has fallen into the hollow body 1 to be discharged to the outside of the inhaler. The porous plate 12 need not necessarily be limited to being a molded part made of synthetic resin material, and may be a screen-like woven material for example.

Operation of the inhaler of this embodiment will now be described.

Referring to the arrangement wherein the hollow body 1 of the inhaler, the capsule holding portion 2, the inhaling section 9 and the porous plate 12 are assembled to one another as shown in FIGS. 1 to 4, the capsule 3 containing powdered preparations is inserted into the capsule insertion hole 4 of the capsule holding portion 2. At this time, the capsule head is held by the capsule insertion hole 4, and the capsule barrel is inserted and projected into the bent section **1*b* in the axial direction thereof in such a manner that at least the forward end of the capsule barrel is inserted and projected into the bent section 1*b* of the hollow body 1 in the axial direction thereof by a dimension capable of satisfactorily abutting against the abutting ridge 6 of the bent section 1*b***.

When, in this state, the patient holds the hollow barrel section **1*a* of the hollow body 1 and the capsule holding portion 2 in his right and left hands, respectively, and rotates the hollow body 1 and the capsule barrel relative to each other, the capsule barrel being the portion of the capsule 3 inserted and projected in the capsule holding portion 2 to abut against the abutting ridge 6 of the hollow body 1. During this operation, the capsule 3 receives a force for separating the capsule barrel from the capsule head, whereby the capsule barrel is separated from the capsule head held by the capsule insertion hole 4 of the capsule holding portion 2. Thus only the capsule barrel falls into the hollow body 1. At this time, at least part of the powdered preparations in the capsule 3 are discharged from the capsule barrel into the hollow body 1 of the inhaler. However, the powdered preparations discharged into the hollow body 1 are prevented from leaking to the outside of the hollow body 1 because the hollow body 1** is of a bent form.

Subsequently, when the patient holds the inhaler, applies his mouth to the tapered portion of the inhaling section 9 to put it into his mouth and inhales, external air flows into the inhaler through the air flow-in openings 5 of the capsule holding portion 2 due to the inhaling force of the patient. The powdered preparations in the inhaler are thus inhaled into the oral cavity of the patient together with the intake air through the pores 13 of the porous plate 12, and adhere to the trachea, bronchi and pulmonary cells of the patient. The intake air, after being taken in through the air flow-in openings 5, reaches a turbulent flow state in the hollow body 1 of the inhaler. This turbulent flow state can be very smoothly and readily formed because the inhaler is of the bent form.

As a consequence, due to the turbulent flow, the capsule barrel, which has fallen into the hollow body 1, strikes the inner wall surface of the hollow body 1 from various directions and rebounds in the hollow body 1. The powdered preparations remaining in the capsule barrel are thus discharged into the hollow body 1 and inhaled into the oral cavity of the patient from the hollow body 1 through the porous plate 12 and the inhaling section 9. Additionally, the capsule barrel which has fallen into the hollow body 1 is not passed through the pores of the porous plate 12 and is prevented from being sucked out of the inhaler together with the intake air.

As described above, in this embodiment, the hollow body 1 of the inhaler has a bent configuration such that the hollow barrel section **1*a* and the bent section 1*b* are inclined at the angle $\alpha$ to each other. Thus the turbulent flow in the inhaler can be readily and reliably formed and the powdered preparations in the capsule 3** can be reliably inhaled into the oral cavity of the patient from the inhaler. Accordingly, the powdered preparations do not remain in the inhaler or the capsule and are effectively inhaled into the oral cavity of the patient, so that an insufficient dosage and wasteful preparations can be prevented from occurring.

It has been found from empirical studies made by the inventors that the following arrangements make the inhaler particularly useful.

First, as for the angle $\alpha$ made by the axes of the hollow barrel section **1*a* and the bent section 1*b* of the hollow body 1, the operating maneuvers of the capsule barrel in the inhaler are not brisk when the angle $\alpha$ is 90 degrees. The functional advantage of the bent form can be achieved when the angle $\alpha$ is within the range from 30 to 80 degrees, and the operating manoeuvres of the capsule barrel become brisker when the angle $\alpha$ is within the range from 45 to 60 degrees. Particularly, when the angle $\alpha$ was set at 60 degrees, the turbulent flows were reliably formed in the hollow body 1, whereby the operating maneuvers of the capsule barrel in the hollow body 1 were performed very briskly, so that it was possible to inhale the powdered preparations in the inhaler efficiently within a short period of time. Moreover, by setting the angle $\alpha$ at the values as described above, such problems were effectively prevented from occurring that the powdered preparations in the hollow body 1 were recirculated into the capsule head held by the capsule insertion hole 4** and remained therein. Additionally, when the angle $\alpha$ was set at a value smaller than 30 degrees, the disadvantages inherent to the conventional straight-lined inhaler were presented.

As for the length of the hollow barrel section **1*a* of the hollow body 1 of the inhaler; i.e. a length l from one end of the hollow barrel section 1*a* to a boundary portion between the hollow barrel section 1*a* and the bent section 1*b* on the inner side in the bending direction of the bent section 1*b*, was preferably made to be 1.5–3.5 cm. In particular, it was found that, by making the length l to be 2.5–3.0 cm, the operating maneuvers of the capsule barrel, the inhaling efficiency of the powdered preparations and the like were highly satisfactory. The inner diameter of the hollow body 1** in that case was about 2.1 cm for an example.

Figure 7A:
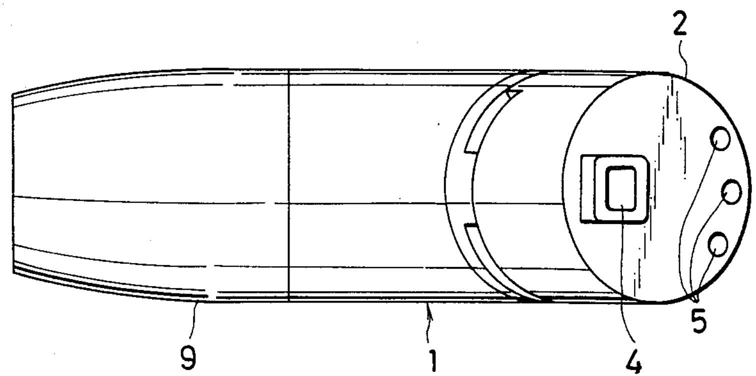
FIGS. 7(*a*) and 7(*b*) are views showing the positional relationship between the inhaler and the air intake openings during inhaling, respectively.
Figure 7B:
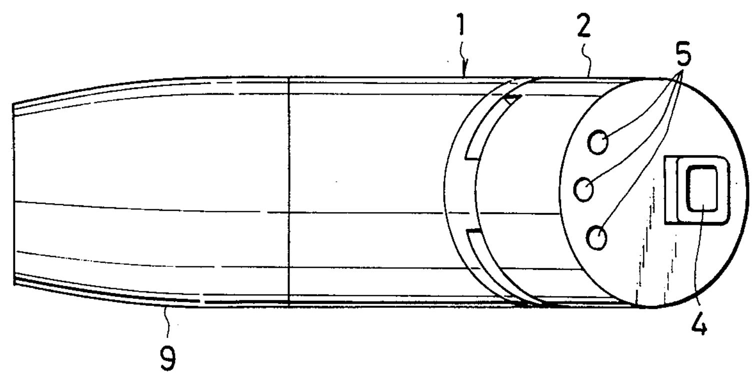

Further, when the inventors studied the forms and arrangements of the air intake openings 5, the following results were obtained. Description will hereunder be given of these results with reference to FIGS. 5 to 7.

Figure 5A:
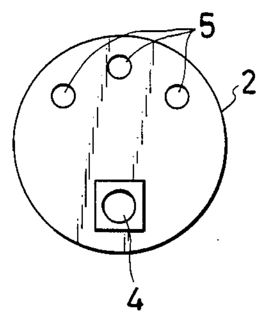
FIGS. 5(*a*), 5(*b*), 5(*c*) are views showing embodiments of forms and arrangements of air intake openings usable in the present invention, respectively.
Figure 5B:
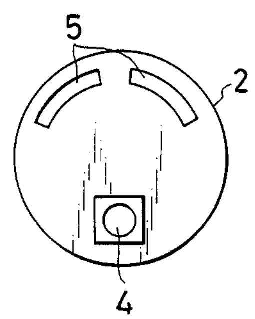
Figure 5C:
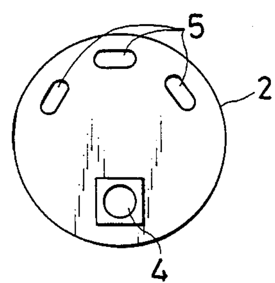
Figure 6A:
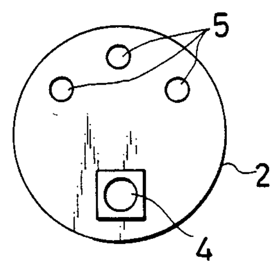
FIGS. 6(*a*), 6(*b*), 6(*c*) and 6(*d*) are views showing various comparative examples of forms and arrangements of air intake openings, respectively.
Figure 6B:
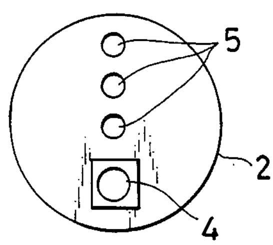
Figure 6C:
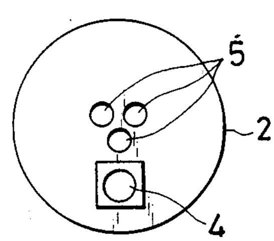
Figure 6D:
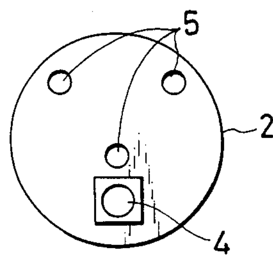

More specifically, FIGS. 5(*a*), 5(*b*) and 5(*c*) show various embodiments of the air intake openings applicable to the present invention, respectively.

First, the air intake openings 5 in the embodiment shown in FIG. 5(*a*) are constructed such that three circular holes are arranged arcuately with one another at regular intervals along and close to the outer periphery of an end face of the capsule holding portion 2 at positions substantially diametrically opposite to the capsule insertion hole 4. The diameter of each air intake opening 5 is 1.5–4.0 mm, preferably about 3.5 mm. The inhaler of this type is indicated as an L type in TABLE 1.

the prior art. As apparent from TABLE 1, each of the inhalers according to the present invention each has a low rate at which the powdered preparations remain in the inhaler and the capsule as compared with the prior art. Thus a highly satisfactory rate of scattering, i.e. a highly satisfactory rate of inhaling to the outside of the inhaler can be attained.

The inventors also conducted experiments on the influences rendered to powder scattering by the forms and arrangements of the air intake openings 5.

The forms of the air intake openings 5 studied under the experiments are shown in FIGS. 6(*a*), 6(*b*), 6(*c*) and 6(*d*) and correspond to A, B, C and D in TABLE 2. As apparent from TABLE 2, the most satisfactory rate of scattering (rate of inhaling) was obtained by the form and arrangement of the air intake openings 5 shown in FIG. 6(*a*). In contrast thereto, the arrangement of FIG. 6(*c*), wherein the air flow-in openings 5 have a concentrated arrangement in the center of the end face of the capsule holding portion 2, shows the lowest rate of scattering. In general, the closer to the center the air flow-in openings 5 are arranged, the fewer turbulent flows are formed, thus lowering the rate of scattering.

Further, the inventors conducted experiments on the influences rendered to the powder scattering by the positions of the air intake openings 5 relative to the hollow body 1. The results of experiments are also shown in TABLE 2. More specifically, an "outside" position and an "inside" position of the air intake openings in TABLE 2 indicate cases shown in FIGS. 7(*a*) and 7(*b*), respectively.

TABLE 1

COMPARISONS OF POWDER SCATTERING PROPERTIES BETWEEN INHALERS

| INHALERS OF THIS INVENTION | | NO. OF SAMPLES n | RATE OF REMAINING IN INHALER | RATE OF REMAINING IN CAPSULE HEAD | RATE OF REMAINING IN CAPSULE BARREL | [%] RATE OF SCATTERING |
|---|---|---|---|---|---|---|
| L TYPE | LONG BARREL | 3 | 7.6 ± 0.84 | 0.3 ± 0.05 | 3.0 ± 0.22 | 89.1 ± 0.68 |
| | SHORT BARREL | 3 | 7.8 ± 1.25 | 0.3 ± 0.03 | 2.9 ± 0.43 | 89.0 ± 0.79 |
| A TYPE | LONG BARREL | 3 | 8.1 ± 0.40 | 0.2 ± 0.01 | 1.9 ± 0.30 | 89.8 ± 0.30 |
| | SHORT BARREL | 3 | 8.1 ± 0.73 | 0.1 ± 0.07 | 1.3 ± 0.26 | 90.5 ± 0.54 |
| S TYPE | LONG BARREL | 3 | 8.6 ± 0.26 | 0.3 ± 0.01 | 1.8 ± 0.08 | 89.3 ± 0.24 |
| | SHORT BARREL | 3 | 8.5 ± 0.77 | 0.4 ± 0.26 | 2.0 ± 0.33 | 89.1 ± 0.69 |
| PRIOR ART | | 3 | 22.8 ± 0.68 | 4.7 ± 0.40 | 3.6 ± 0.63 | 68.9 ± 0.44 |

The embodiment shown in FIG. 5(*b*) is constructed such that two arcuate slit-shaped air flow-in openings 5 similar to the embodiments shown in FIGS. 1–4 are arranged arcuately with one another at positions diametrically opposite to the capsule insertion hole 4, and the positional relationship between the air intake openings 5 and the capsule insertion hole 4 is different from ones shown in FIGS. 1–4. The inhaler of this type is indicated as an A type in TABLE 1.

The embodiment shown in FIG. 5(*c*) is constructed such that three slot- or tablet-shaped air intake openings 5 are arranged arcuately with one another at positions diametrically opposite to the capsule insertion hole similarly to the case of the circular holes in FIG. 5(*a*). The inhaler of this type is indicated as an S type in TABLE 1.

TABLE 1 shows examples wherein the L type, A type and S type inhalers having the constructions of the air intake openings according to the present invention, are compared with the latter of the aforesaid inhalers of

TABLE 2

INFLUENCE RENDERED TO POWDER SCATTERING BY FORMS OF AIR FLOW-IN OPENINGS

| FORM OF AIR FLOW-IN OPENINGS | POSITION OF AIR FLOW-IN OPENINGS | NO. OF SAMPLES n | RATE OF REMAINING IN VARIOUS PORTIONS [%] | | | RATE OF SCATTERING [%] |
|---|---|---|---|---|---|---|
| | | | INHALER | CAPSULE HEAD | CAPSULE BARREL | |
| A | inside | 3 | 8.45 ± 0.33 | 0.26 ± 0.03 | 1.99 ± 0.09 | 89.3 ± 0.76 |
| | outside | 3 | 9.02 ± 0.53 | 0.35 ± 0.04 | 1.90 ± 0.11 | 88.7 ± 0.87 |
| B | inside | 3 | 15.4 ± 1.22 | 0.30 ± 0.02 | 6.40 ± 0.82 | 77.9 ± 1.30 |
| | outside | 3 | 14.2 ± 0.98 | 0.23 ± 0.04 | 7.20 ± 0.63 | 78.4 ± 1.21 |
| C | inside | 3 | NO POWDER SCATTERED | | | 0 |
| | outside | 3 | 17.3 ± 1.83 | 0.42 ± 0.06 | 7.71 ± 1.23 | 74.6 ± 0.71 |
| D | inside | 3 | 16.5 ± 2.00 | 0.32 ± 0.03 | 4.75 ± 0.66 | 78.4 ± 0.55 |
| | outside | 3 | 16.9 ± 2.19 | 0.45 ± 0.04 | 4.01 ± 0.18 | 78.6 ± 0.81 |

The "outside" position shows the case where inhaling is performed with the air intake openings 5 being positioned on the outer side of the bending direction of the bent section 1*b* of the hollow body 1 of the inhaler, and the "inside" position shows the case of the position contrary to the above.

According to TABLE 2, when the forms of the air intake openings are the ones shown in FIGS. 6(*a*), 6(*b*) and 6(*d*), there is not much difference in the rate of scattering between the "inside" position and the "outside" position. However, in the case of FIG 6(*c*), when the air intake openings 5 are located at the "inside" position, the powder was not scattered at all.

When the inventors ascertained by experiments the rates of powder scattering in the cases where the air intake openings 5 are located at the "inside" position, the "outside" position or the side positions for the L type, A type and S type inhalers in TABLE 1, respectively, the following results were obtained.

First, with the L type inhaler (shown in FIG. 5(*a*)), the operating maneuvers of the capsule barrel were better when the air intake openings 5 were located at the "outside" position but not at the "inside" position. Furthermore, when th air intake openings were located at peripheral positions slightly inwardly of the "outside" position, i.e. the side position, satisfactory results were obtained.

Next, with the A type inhaler (shown in FIG. 5(*b*)), regardless of the positions of the air intake openings 5, the operating maneuvers of the capsule barrel were good, a satisfactory scattering performance was obtained, and particularly, the "outside" position was excellent.

Furthermore, with the S type inhaler (shown in FIG. 5(*c*)), when the air intake openings 5 are located at the "outside" position, the operating maneuvers of the capsule barrel were highly satisfactory. However, when the air intake openings 5 are located at the "inside" position, the operating manoeuvres of the capsule barrel were not briskly performed.

Consequently, putting all the above study results together, it becomes apparent that the optimum requirements for the inhaler according to the present invention include the angle $\alpha$ formed by the axis of the hollow barrel section 1*a* of the hollow body 1 and the axis of the bent section 1*b* is 60 degrees, the length l of the hollow barrel section 1*a* on the inner side in the bending direction is 2.5–3.0 cm, two air intake openings 5 of arcuate slit shapes are used with the opening area being about 0.31 $cm^2$, and the positions of the air flow-in openings 5 are on the outer side of the bent section 1*b* during inhaling.

Embodiment 2

Figure 8:
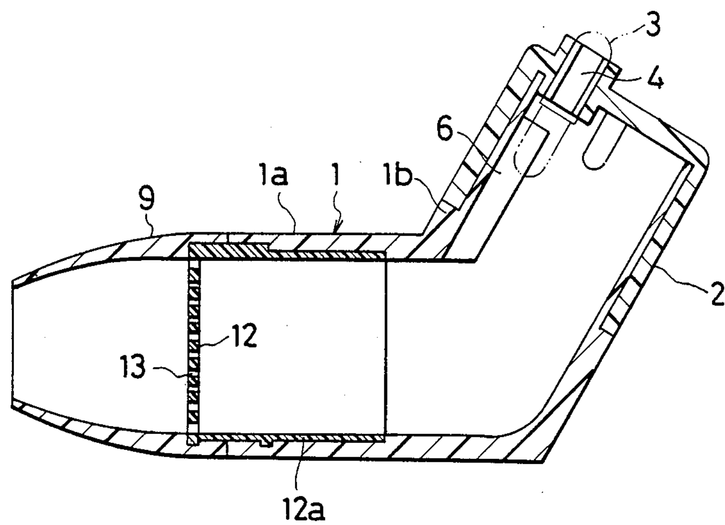
FIG. 8 is a sectional view showing another embodiment of the inhaler according to the present invention.
Figure 9:
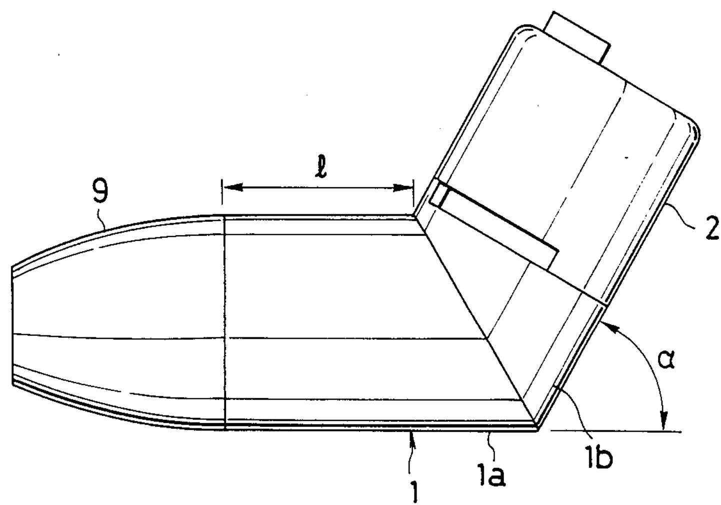
FIG. 9 is a front view thereof.

FIGS. 8 and 9 are sectional and front views showing another embodiment of the inhaler according to the present invention.

In this embodiment, the porous plate 12 is integrally formed on a cylindrical portion 12*a* to provide a cup-shaped member, and the hollow barrel section 1*a* of the hollow body 1 and the inhaling section 9 are indirectly connected to each other through this cup-shaped member.

In this embodiment, the inhaler as a whole is of a bent form, so that the powdered preparations can be prevented from leaking out of the inhaler when the capsule is separated, the operating maneuvers of the capsule barrel can be improved and the rate of scattering of the powder, i.e. the rate of inhaling can be improved during inhaling.

Additionally, the present invention need not necessarily be limited to the above embodiments, and various other modifications can be adopted.

For example, in the above embodiments, the bent section 1*b* of the hollow body 1 is straight-lined, however, this may be curved.

Furthermore, the whole or a part of the inhaler may be made of a transparent or a semi-transparent synthetic resin material.

Further, the forms or arrangements of the air intake openings 5 may be changed to ones other than the above.

According to the present invention, the following outstanding advantages can be attained.

(1) The inhaler according to the present invention comprises:

a hollow body including a hollow barrel section having a predetermined length and a hollow bent section connected to one end of this hollow barrel section and having an axis inclined at a predetermined angle to an axis of the hollow barrel section;

a capsule holding portion relatively rotatably connected to the bent section of the hollow body and formed at portions of the end face thereof with a capsule insertion hole and air intake openings;

abutting means projected from the inner surface of the bent section of the hollow body, for abutting against a capsule's portion inserted and projected into the hollow body when the capsule is inserted into and held by the capsule insertion hole of the capsule holding portion and the capsule holding portion is rotated relative to the hollow body, so as to divide the capsule into two;

a hollow inhaling section directly or indirectly connected to the outer end of the hollow barrel section; and capsule discharging preventive means formed with pores to pass a material contained in the capsule therethrough, for preventing a capsule's portion, which has fallen into the hollow body, from being discharged to the outside of the inhaling section; so that turbulent flows can be readily formed in the inhaler during inhaling, the operating maneuvers of the capsule portion in the inhaler can be improved, and the material contained in the inhaler can be reliably inhaled into the oral cavity of the user from the inhaler without the material remaining in the capsule portion and the inhaler.

(2) With the arrangement described in Item (1), the material contained in the capsule, which has fallen into the inhaler from the capsule, can be prevented from leaking to the outside of the inhaler when the capsule is divided into two.

(3) With the arrangement described in Item (1), the material contained in the capsule, which has fallen into the inhaler from the capsule, can be prevented from recirculating into the capsule head being open in the inhaler and remaining therein as it is during inhaling.

(4) With the arrangement described in Item (1), such a disadvantage can be obviated wherein the inhaler rolls off a flat surface suc as a table.

What is claimed:

1. An inhaler for use with a capsule of non-pressurized contents comprising, a hollow body including a hollow barrel section having a predetermined length, and a first central longitudinal axis, said hollow barrel section having opposite end portions, one of said end portions being a free end portion, said hollow body further including a hollow bent section having an inner surface, and being connected to one end of said hollow barrel section said hollow bent section having a second central longitudinal axis inclined at a predetermined angle in the range of 30–80 degrees to the first central longitudinal axis of the hollow barrel section such that said hollow barrel section and said hollow bent section define a continuous internal flow path having a first flow path section along said first central longitudinal axis and a second flow path section along said second central longitudinal axis;

a capsule holding portion rotatably joined to said bent section of the hollow body and having an end face formed with a capsule insertion opening and air intake openings, said capsule insertion opening adapted to hold said capsule of non-pressurized contents having a capsule head and a capsule barrel wherein the capsule head is held in the capsule insertion opening and the capsule barrel freely projects into the second flow path section but does not project into the first flow path section;

abutting means projecting from the inner surface of said bent section of the hollow body, for abutting against the capsule barrel when the capsule holding portion is rotated a predetermined amount relative to the hollow body, so as to separate said capsule barrel from said capsule head to permit free fall of the capsule barrel and the non-pressurized capsule contents through the second flow path section into the first flow path section;

a hollow inhaling section provided at the free end of the hollow barrel section for suction communication with the first and second flow path sections of said internal flow path;

capsule discharge preventive means formed with pores to pass the non-pressurized capsule contents therethrough, and for preventing said capsule barrel, which has fallen into the first flow path section from being discharged to the outside of the inhaling section;

said capsule head held by said capsule insertion opening being opened in said second flow path section and inclined to the first central longitudinal axis of said first flow path section; and said air intake openings including at least one opening radially spaced from the second central longitudinal axis of said bent section.

2. An inhaler as set forth in claim 1 wherein the angle of the second central longitudinal axis of said bent section to the first central longitudinal axis of said hollow barrel section is 45°-60°.

3. An inhaler as set forth in claim 2 wherein the angle of the second central longitudinal axis of said bent section to the first central longitudinal axis of said hollow barrel section is 60°.

4. An inhaler as set forth in claim 1, wherein said air intake openings are arcuate slit-shaped.

5. An inhaler as set forth in claim 4, wherein said air intake openings are formed of two arcuate slit-shaped holes and the total opening area of said holes is about 0.3 $cm^2$.

6. An inhaler as set forth in claim 1, wherein said air intake openings are generally slot-shaped.

7. An inhaler as set forth in claim 6, wherein said generally slot-shaped air intake openings are arranged arcuately with one another at positions close to the outer periphery of the end face of said capsule holding portion.

8. An inhaler as set forth in claim 1, wherein said air intake openings are circular in shape.

9. An inhaler as set forth in claim 8, wherein said air intake openings are formed of three circular holes and each of said holes is 1.5-4.0 mm in diameter.

10. An inhaler as set forth in claim 9, wherein said three circular air intake openings are arranged arcuately with one another at positions close to the outer periphery of an end face of said capsule holding portion and each of said holes is about 3.5 mm in diameter.

11. An inhaler as set forth in claim 1, wherein said abutting means is integrally formed on the inner surface of said bent section.

12. An inhaler as set forth in claim 1, wherein a length from one end of said hollow barrel section to a boundary portion between said hollow barrel section and said hollow bent section on the inner side in the bending direction of said hollow bent section is 1.5-3.5 cm.

13. An inhaler as set forth in claim 12, wherein the length from one end of said hollow barrel section to the boundary portion between said hollow barrel section and said bent section on the inner side in the bending direction of said bent section is about 2.5-3.0 cm.

14. An inhaler as set forth in claim 1, wherein said capsule discharging preventive means is formed of a molded synthetic resin having a multitude of pores.

15. An inhaler as set forth in claim 1, wherein said inhaler is made of an opaque synthetic resin material.

16. An inhaler as set forth in claim 1 wherein said hollow bent section and said hollow barrel section define a continuous hollow chamber and permit development of a turbulent suction within said hollow chamber when mouth suction is applied to said inhaling section.

17. An inhaler as set forth in claim 1 wherein said inhaler is made of a transparent synthetic resin material.

18. An inhaler for use with a capsule of non-pressurized contents comprising, a hollow body including a barrel section having a first central longitudinal axis and a bent section, said barrel section and said bent section defining a continuous hollow flow path chamber characterized by a straight hollow flow path portion corresponding to the barrel section and an inclined hollow flow path portion corresponding to the bent section, said bent section having a second central longitudinal axis inclined at an angle in the range of 30°-80° to the first central longitudinal axis of the barrel section, a capsule holding portion at one end of the hollow body rotatably joined to said bent section and having an end face, a capsule insertion opening formed in said end face for holding said capsule of non-pressurized contents in a position wherein a portion of the capsule projects into the inclined hollow flow path portion, but does not project into the straight hollow flow path portion, air intake openings formed in said end face spaced from said capsule insertion opening, said bent section having an inner surface, abutting means projecting from said inner surface for abutting against the projecting portion of the capsule held in the capsule insertion opening when the capsule holding portion is rotated a predetermined amount relative to the hollow body to separate the projecting portion of the capsule from the held portion and permit the projecting portion of the capsule to drop through the inclined hollow flow path portion into the straight hollow flow path portion to permit movement of the projecting capsule portion and the non-pressurized capsule contents throughout the inclined hollow flow path portion and the straight hollow flow path portion, said hollow body further including a hollow inhalation section continuous with the barrel section, said inhalation section having an inhalation opening communicating through the inhalation section with the hollow flow path chamber and the air intake openings to permit a suction flow toward the inhalation opening from the air intake openings through the hollow flow path chamber, and, porous means in said hollow body spaced from said inhalation opening, whereby the inclined hollow flow path portion and the straight hollow flow path portion of the hollow flow path chamber facilitate development of a turbulent suction flow within the inclined hollow flow path portion and the straight hollow flow path portion when mouth suction is applied at said inhalation opening, and said porous means block passage of said projecting capsule portion to said inhalation opening during mouth suction and permit passage of the non-pressurized capsule contents through the inclined hollow flow path portion and the straight hollow flow path portion during mouth suction for discharge of the non-pressurized capsule contents through the inhalation opening.

* * * * *

UNITED STATES PATENT AND TRADEMARK OFFICE

CERTIFICATE OF CORRECTION

PATENT NO. : 4,846,168

DATED : July 11, 1989

INVENTOR(S) : Kenji ABIKO et al.

It is certified that error appears in the above-identified patent and that said Letters Patent is hereby corrected as shown below:

At column 2, line 35, add --(1)-- at the end of the sentence before "."

At column 2, line 36, delete "(1)"

At column 4, line 9, change "length 1" to --length ℓ --

At column 4, line 66, after "patient" 2nd occurrence insert --sucks--

At column 6, line 20, change "configuration" to --construction--

At column 6, lines 60 and 66, change "length 1" to --length ℓ --

At column 9, line 40, change "length 1" to --length ℓ --

At column 10, line 55, change "suc" to --such--.

Signed and Sealed this

Twenty-second Day of May, 1990

*Attest:*

HARRY F. MANBECK, JR.

*Attesting Officer* *Commissioner of Patents and Trademarks*